United States Patent
Choi et al.

(10) Patent No.: US 11,403,864 B2
(45) Date of Patent: Aug. 2, 2022

(54) METHOD AND APPARATUS FOR ACQUIRING INFORMATION ON SHAPE OF OBJECT

(71) Applicant: Snow Corporation, Seongnam-si (KR)

(72) Inventors: Sangho Choi, Seongnam-si (KR); Byung-Sun Park, Seongnam-si (KR); Junghwan Jin, Seongnam-si (KR); Wonhyo Yi, Seongnam-si (KR); Hyeongbae Shin, Seongnam-si (KR); Seongyeop Jeong, Seongnam-si (KR); Sungwook Kim, Seongnam-si (KR); Noah Hahm, Seongnam-si (KR); Jimin Kim, Seongnam-si (KR)

(73) Assignee: SNOW CORPORATION, Gyeonggi-Do (KR)

( * ) Notice: Subject to any disclaimer, the term of this patent is extended or adjusted under 35 U.S.C. 154(b) by 270 days.

(21) Appl. No.: 16/584,162

(22) Filed: Sep. 26, 2019

(65) Prior Publication Data
US 2020/0019766 A1 Jan. 16, 2020

Related U.S. Application Data

(63) Continuation of application No. PCT/KR2017/003273, filed on Mar. 27, 2017.

(51) Int. Cl.
*G06V 40/00* (2022.01)
*G06Q 10/00* (2012.01)
(Continued)

(52) U.S. Cl.
CPC .............. *G06V 40/10* (2022.01); *G06Q 10/20* (2013.01); *G06Q 30/0631* (2013.01); *G06T 7/50* (2017.01);
(Continued)

(58) Field of Classification Search
None
See application file for complete search history.

(56) References Cited

U.S. PATENT DOCUMENTS

| 2002/0138170 A1* | 9/2002 | Onyshkevych | G06Q 30/06 700/130 |
| 2003/0076318 A1* | 4/2003 | Shaw-Weeks | G06T 17/00 345/419 |

(Continued)

FOREIGN PATENT DOCUMENTS

| CN | 102467235 A | 5/2012 |
| CN | 105740839 A | 7/2016 |

(Continued)

OTHER PUBLICATIONS

Japanese Office Action dated Sep. 23, 2020 by the Japanese Patent Office corresponding to Japanese Patent Application No. 2019-554403.

(Continued)

*Primary Examiner* — Matthew C Bella
*Assistant Examiner* — Brian D Shin
(74) *Attorney, Agent, or Firm* — Harness, Dickey & Pierce, PLC

(57) ABSTRACT

Provided are a method and an apparatus wherein an object is distinguished from the background of the object by using a sensor unit including at least one sensor, the distances to measurement points of the background and/or the object are measured, and information on the shape of at least one part constituting the object is acquired on the basis of the measured distances.

19 Claims, 9 Drawing Sheets

(51) Int. Cl.
| | |
|---|---|
| *G01S 7/48* | (2006.01) |
| *G06V 40/10* | (2022.01) |
| *G06T 7/62* | (2017.01) |
| *G06T 7/50* | (2017.01) |
| *G06Q 30/06* | (2012.01) |
| *G06V 20/20* | (2022.01) |
| *G01S 7/539* | (2006.01) |

(52) U.S. Cl.
CPC ................ *G06T 7/62* (2017.01); *G06V 20/20* (2022.01); *G01S 7/4802* (2013.01); *G01S 7/539* (2013.01); *G06T 2207/10028* (2013.01); *G06T 2207/30196* (2013.01)

(56) References Cited

U.S. PATENT DOCUMENTS

| | | | |
|---|---|---|---|
| 2010/0023421 A1 | 1/2010 | Wannier et al. | |
| 2010/0111370 A1 | 5/2010 | Black et al. | |
| 2011/0040217 A1 | 2/2011 | Centen | |
| 2012/0076361 A1* | 3/2012 | Fujiyoshi | G06K 9/00369 |
| | | | 382/103 |
| 2015/0269739 A1* | 9/2015 | Ho | G06T 7/194 |
| | | | 382/164 |
| 2016/0292497 A1* | 10/2016 | Kehtarnavaz | G06K 9/6292 |
| 2016/0292523 A1 | 10/2016 | Chuang et al. | |

FOREIGN PATENT DOCUMENTS

| | | |
|---|---|---|
| JP | 2003-082515 A | 3/2003 |
| JP | 2005-165531 A | 6/2005 |
| JP | 2009-536731 A | 10/2009 |
| JP | 2010-084263 A | 4/2010 |
| JP | 2010-524090 A | 7/2010 |
| JP | 2011-253521 A | 12/2011 |
| JP | 2016-040649 A | 3/2016 |
| KR | 20120051212 A | 5/2012 |
| KR | 20130136090 A | 12/2013 |
| KR | 10-2014-0077820 A | 6/2014 |
| KR | 20140118185 A | 10/2014 |

OTHER PUBLICATIONS

Korean Office Action dated Mar. 24, 2021 for Korean Patent Application No. 10-2019-7025879.

International Search Report dated Sep. 13, 2017, issued in corresponding International Application No. PCT/KR2017/003273.

Chinese Office Action dated Aug. 16, 2021 by the Chinese Patent Office for corresponding Chinese patent application No. 201780089269.3.

Chinese Office Action dated Jan. 13, 2022 for Chinese Patent Application No. 201780089269.3.

* cited by examiner

METHOD AND APPARATUS FOR ACQUIRING INFORMATION ON SHAPE OF OBJECT

CROSS-REFERENCE TO RELATED APPLICATIONS

This application is a continuation of PCT International Application No. PCT/KR2017/003273, which has an international filing date of Mar. 27, 2017, the entire contents of which are incorporated herein by reference.

BACKGROUND

Technical Field

Example embodiments relate to a method and/or apparatus for acquiring information on a shape of an object using a sensor. For example, at least some example embodiments relate to a method and/or apparatus that may acquire information on a shape of an object that is a body using a sensor and recommend an item suitable for the body.

Related Art

Conventionally, in terms of measuring or predicting a size of an object included in a subject or a portion that constitutes the object, an operation of tracking a movement of a moving object may be performed to identify the object and a background and to calculate a size of the object. Alternatively, the size of the object may be measured by scanning the object with a dedicated scanner.

However, since tracking a moving object may involve a time-based tracking action, this method may not be efficient to determine a size of the object. Also, the method based on tracking of the moving object may not meet the requirements of high precision that is required to determine the size of the object.

In the meantime, a method of determining a size of an object using a dedicated scanner may require the dedicated scanner to determine the size of the object and thus, may not be readily used for universal purpose.

The above-noted information is merely provided to help understanding and may include content that does not form a part of the related art and may not include what could be offered to those skilled in the art.

SUMMARY

At least some example embodiments are directed to a method of acquiring information on a shape of an object. In some example embodiments, the method includes distinguishing, via at least one sensor, the object from a background around the object; measuring, via the at least one sensor, a distance from at least one measurement point among at least one point of the background and at least one point of the object to the at least one sensor; and acquiring information on a shape of at least one portion of the object based on at least the distance.

In some example embodiments, the at least one sensor includes a depth sensor, and the distinguishing includes distinguishing the object from the background by verifying the background and an outline of the object using the depth sensor.

In some example embodiments, the at least one sensor includes a distance sensor, and the measuring includes measuring the distance based on a time of flight (ToF) from the measurement point using the distance sensor.

In some example embodiments, the information on the shape includes a size of the portion, the measuring includes measuring distances from a plurality of measurement points of the portion to the at least one sensor, and the acquiring includes acquiring information on the size of the portion based on angles associated with the plurality of measurement points and the distances from the plurality of measurement points to the at least one sensor.

In some example embodiments, the information on the size of the portion includes at least one of a length and a width of the portion.

In some example embodiments, the distinguishing includes distinguishing a background element from a remaining portion of the background based on at least one of a height of at least one background element of the background and pattern information.

In some example embodiments, the distinguishing includes determining the background element as one of a plurality of set types of background elements in response to a degree of matching between data represented by the background element and the pattern information of the one of the plurality of set types of background elements being greater than or equal to a desired value.

In some example embodiments, the object is a body, the portion is a part of the body, and the information on the shape indicates at least one of a shape, a length, and a width of at least the part of the body.

In some example embodiments, the method further includes determining a body type of the body based on the information on the shape.

In some example embodiments, the body includes a plurality of parts, and the determining of the body type includes determining the body type of the body based on the information on the shape of at least two parts among the plurality of parts and the information on the shape of a predetermined part among the plurality of parts.

In some example embodiments, the method further includes providing recommendation information on at least one item among clothes and accessories wearable to the part, based on the information on the shape.

In some example embodiments, the providing of the recommendation information includes providing the recommendation information on the at least one item based on a body type of the body, the body type determined based on the information on the shape.

In some example embodiments, the providing of the recommendation information includes providing the recommendation information on at least one item based on statistical information associated with the body type of the body.

In some example embodiments, the providing of the recommendation information includes providing the recommendation information on at least one item based on size information of the part, the size information being determined based on the information on the shape.

In some example embodiments, the method further includes determining whether to recommend repair of the item by comparing a measurement of the item and the information on the shape; and providing repair information on the item in response to determining to recommend the repair.

In some example embodiments, the determining whether to recommend the repair of the item is based on style information set by a user.

Some example embodiments relate to a non-transitory computer-readable record medium storing a program that, when executed by processing circuitry, configures the processing circuitry to perform a method of acquiring information on a shape of an object.

Some example embodiments relate to an electronic device includes at least one sensor; and processing circuitry configured to, distinguish, via the at least one sensor, an object from a background around the object, measure a distance from at least one measurement point among at least one point of the background and at least one point of the object to the at least one sensor, and acquire information on a shape of at least one portion of the object based on at least the distance.

In some example embodiments, the object is a body, the portion is a part of the body, and the information on the shape includes at least one of a shape, a length, and a width of at least a portion of the part, and the processing circuitry is further configured to determine a body type of the body based on the information on the shape.

In some example embodiments, the object is a body, the portion is a part of the body, and the information on the shape includes at least one of a shape, a length, and a width of at least the part of the body, and the processing circuitry is further configured to provide recommendation information on at least one item among clothes and accessories wearable to the part of the body, based on the information on the shape.

DETAILED DESCRIPTION

Hereinafter, example embodiments will be described with reference to the accompanying drawings.

Figure 1:
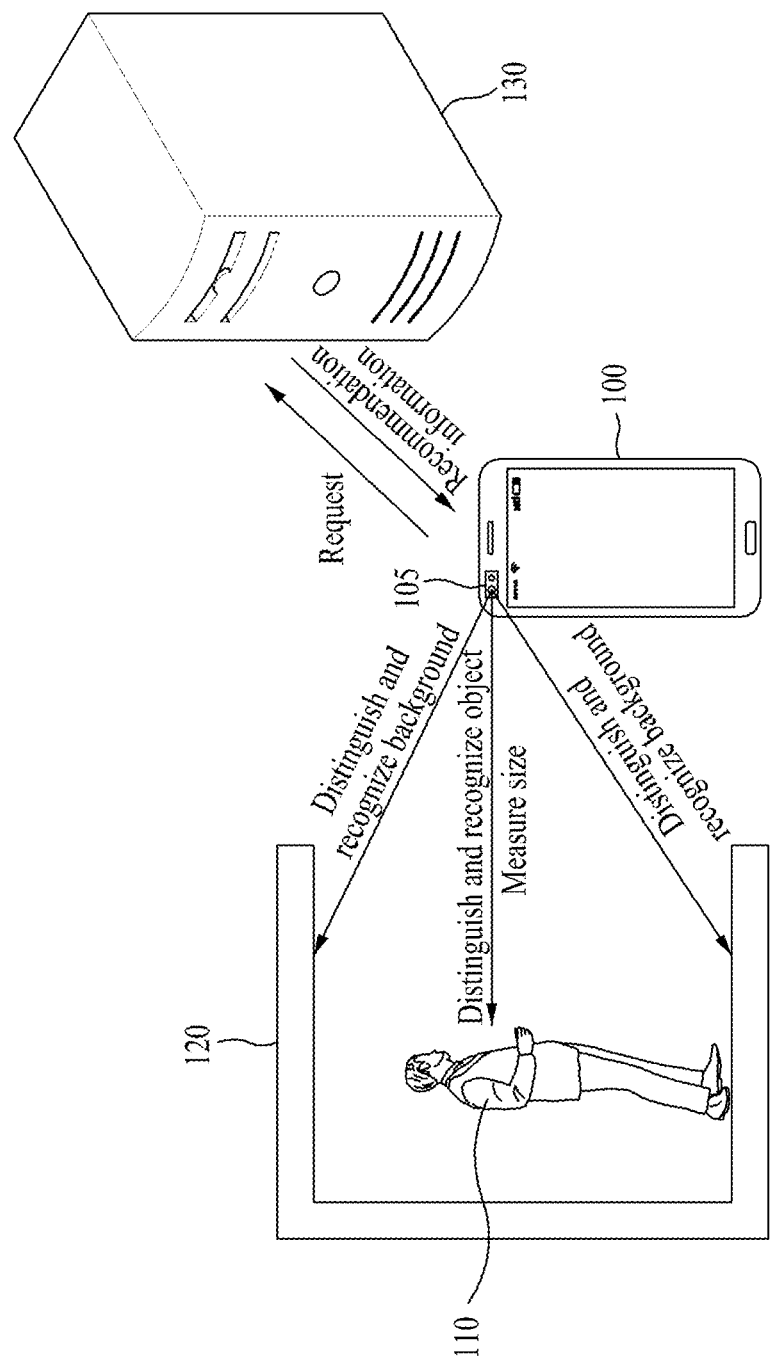
FIG. 1 illustrates a method of acquiring information on a shape of an object using a sensor unit and providing recommendation information on a suitable item based on the acquired information on the shape according to an example embodiment.

FIG. 1 illustrates a method of acquiring information on a shape of an object using a sensor unit and providing recommendation information on a suitable item based on the acquired information on the shape according to an example embodiment.

Referring to FIG. 1, an electronic device 100 may recognize and identify an object 110 corresponding to a subject and a background 120 present around the object 110 using a sensor unit 105 included in the electronic device 100, measure a distance from the sensor unit 105 to at least one measurement point of the object 110 and/or the background 120, and acquire information on a shape of the object 110 based on the measured distance. Acquiring information on the shape may be understood as that the electronic device 100 calculates and provides information on the shape of the object 110 based on the measured distance.

The acquired information on the shape of the object 110 may be information on a shape of at least one portion that constitutes the object 110. For example, the information on the shape of the object 110 may be information on a size of the object 110 or at least one portion that constitutes the object 110.

The electronic device 100 may request, for example, a server 130 present outside for information on an item suitable for the acquired information on the size based on the acquired information on the size, and may receive information on the suitable item from the server 130 as recommendation information. The electronic device 100 may provide the received recommendation information to a user. Although it is not illustrated, the recommendation information may be provided from not the server 130 present outside but as information stored in the electronic device 100.

The electronic device 100 may be configured to acquire information on a size of the object 100 or at least one portion that constitutes the object 100, as a device that includes the sensor unit 105. For example, the electronic device 100 may be a user terminal such as a smartphone, as illustrated in FIG. 1. A detailed configuration of the electronic device 100 and operations and functions of elements that constitute the electronic device 100 are further described with reference to FIG. 2.

The object 110 may refer to an object of which information on a shape is to be acquired by the electronic device 100. For example, the object 110 may correspond to a body of a user of the electronic device 100 or a portion of the body. That is, information on the shape acquired by the electronic device 100 may include part shape information on at least one part that constitutes the body.

The background 120 may be a remaining portion excluding the object 110 from a portion that is identified using the sensor unit 105 of the electronic device 100. For example, the background 120 may include a ceiling, a floor, and a wall. Also, the background 120 may include any things excluding the object 110, for example, a door, a light, and various decorations. The electronic device 100 may distinguish the object 110 from the background 120 by verifying background element(s) included in the background 120, and may acquire information on a shape of at least one portion that constitutes the object 110 with respect to the distinguished object 110.

In response to a request from the electronic device 100 or as information on the shape of at least one portion constituting the object 110 is acquired, the server 130 may provide recommendation information on an item suitable for the object 110 to the electronic device 100 based on information on the shape. For example, when the object 110 is a body, the server 130 may provide the electronic device 100 with recommendation information on at least one piece of clothes and/or accessories suitable for information on the shape verified for the object 110, that is, a size of the body.

The server 130 may include a database configured to store information on an item associated with the recommendation information. A detailed configuration of the server 130 and operations and functions of elements that constitute the server 130 are further described with reference to FIG. 2.

In the meantime, a method of distinguishing, by the electronic device 100, the object 110 from the background 120 and acquiring information on a shape of the object 110 are further described with reference to FIGS. 3 to 12.

Figure 2:
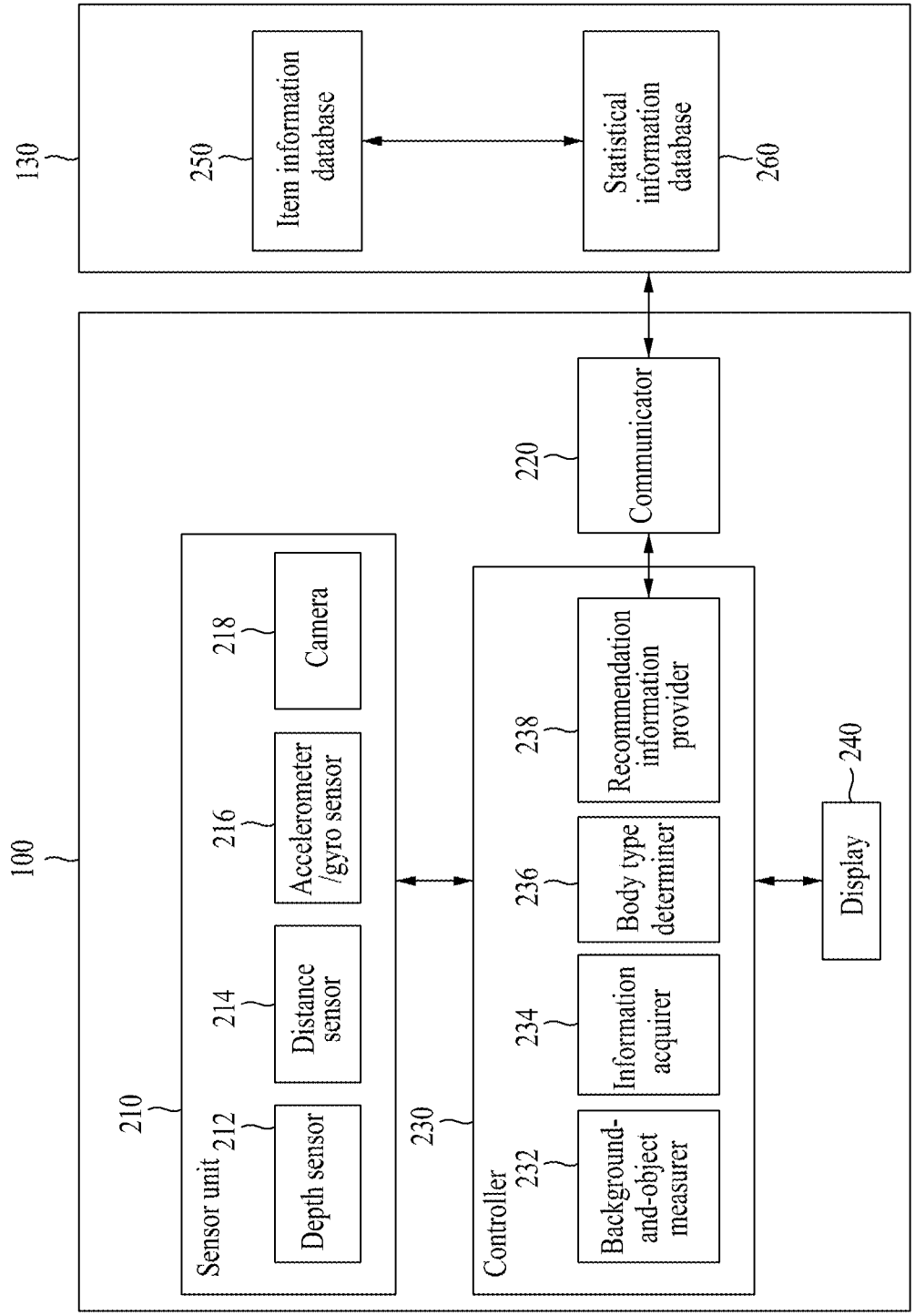
FIG. 2 is a diagram illustrating a configuration of an electronic device configured to acquire information on a shape of an object and a server configured to provide recommendation information on an item according to an example embodiment.

FIG. 2 is a diagram illustrating a configuration of an electronic device configured to acquire information on a shape of an object and a server configured to provide recommendation information on an item according to an example embodiment.

Referring to FIG. 2, the electronic device 100 of FIG. 2 may correspond to the electronic device 100 of FIG. 1. Although FIG. 1 illustrates the electronic device 100 as a smartphone and a device similar thereto, the electronic device 100 may be, for example, a personal computer (PC), a notebook (laptop computer), a laptop computer, a tablet, an Internet Of Things (IoT) device, and a wearable computer, and may correspond to any device that includes a sensor unit available to acquire information on a shape of the object 110 in an example embodiment.

The electronic device 100 may include a sensor unit 210, a communicator 220, and a controller 230. Also, the electronic device 100 may further include a display 240 configured to output processed or received information. Also, although not illustrated, the electronic device 100 may further include an input device configured to receive an input of a message or an interaction from a user.

The sensor unit 210 may correspond to the sensor unit 105 of FIG. 1. The sensor unit 210 may include at least one sensor configured to measure/acquire data from the object 110 and the background 120. For example, the sensor unit 210 may include at least one of a depth sensor 212, a distance sensor 214, an accelerometer sensor 216, and a gyro sensor 216. Also, the sensor unit 210 may further include a camera 218 including an image sensor configured to generate an image by photographing the object 110 and the background 120.

The depth sensor 212 may be a device configured to measure/acquire information on a three-dimensional (3D) depth of at least a portion of a subject. For example, the depth sensor 212 may include a light emitter and a light receiver, and may detect a depth image of the subject through light that is emitted from the light emitter. The light emitted from the light emitter may be, for example, an infrared ray. That is, the depth sensor 212 may include an infrared sensor. The depth sensor 212 may generate depth image information using an amount of time used for the light emitted from the light emitter to be reflected and return, that is, time of flight (ToF). The light emitter and the light receiver may be separate from each other. According to a decrease in a distance between the light emitter and the light receiver, an error may be reduced and precise depth image information may be generated.

The distance sensor 214 may refer to a device configured to measure/detect a distance from the distance sensor 214 to at least one measurement point of the subject. Alternatively, the distance sensor 214 may refer to a device configured to measure/detect a distance between two measurement points of the subject. The distance sensor 214 may include at least one of an IR sensor or an ultrasound sensor and a position sensitive device (PSD) sensor. The distance sensor 214 may measure a distance from a measurement point based on ToF from the light or a soundwave (or other waves) emitted from the distance sensor 214 to the measurement point of the subject. The aforementioned depth sensor 212 and distance sensor 214 may be configured as a single sensor. That is, the depth sensor 212 may perform the functionality of the distance sensor 214.

The gyro sensor 216 may refer to a device configured to detect rotation of the electronic device 100 and to measure/acquire information on a position and/or a direction of the electronic device 100.

The accelerometer sensor 216 may refer to a device configured to measure/acquire acceleration data about three axes of x, y, and z axes of the electronic device 100 by detecting a movement of the electronic device 100. Information on a position and/or a direction of the electronic device 100 may be acquired based on data measured/acquired by the accelerometer sensor 216. Referring to FIG. 2, the gyro sensor and the accelerometer sensor may be configured as a single sensor module 216.

The camera 218 may refer to a device configured to generate an image by photographing the subject.

In addition to the aforementioned sensors 212, 214 and 216, and camera 218, the sensor unit 210 may additionally or alternatively include any sensor configured to acquire a distance from a measurement point of the object 110 and/or the background 120. Also, at least a portion of the sensors 212, 214, and 216 and the camera 218 may be configured as an integrated module.

The communicator 220 may refer to a device for communication between the electronic device 100 and another electronic device or the server 130. That is, the communicator 220 may be a hardware module such as a network interface card, a network interface chip, and a networking interface port of the electronic device 100 or a software module such as a network device driver or a networking program, to transmit/receive data and/or information with respect to the electronic device or the server 130.

The controller 230 may manage constituent elements of the electronic device 100 and may execute a program or an application used by the electronic device 100. For example, the controller 230 may be configured to execute an application that runs to acquire information on the shape of the object 110 and to process data received from the server 130 or the other electronic device. Also, the controller 230 may process an operation required to execute the application and process the data.

The controller 230 may be at least one processor of the electronic device 100 or at least one core in the processor. A detailed configuration of the controller 230 is further described below.

The display 240 may include a display device configured to output data input from the user and to output the acquired/calculated information on the object 110, for example, information on a shape of at least one portion constituting the object 110, and recommendation information provided from the server 130. For example, the display 240 may include a touchscreen. That is, the display 240 may include a function of an inputter that is not illustrated. The user of the electronic device 100 may change or select at least one of a setting associated with the electronic device 100, a setting associated with acquirement of information on the shape, and a setting associated with the recommendation information, for example, a setting associated with information required to determine the recommendation information, through the inputter.

In the meantime, although not illustrated, the electronic device 100 may include a storage as a device configured to store data or information. The storage may include any memory or storage device. A program or an application executed by the controller 230 and information related thereto may be stored in the storage. For example, the storage may include at least a portion of the acquired (i.e., calculated) information on the shape of the object 110, information on the background 120 information on other objects 110, and information measured by the sensor unit 210.

Further specifically describing the controller 230, the controller 230 may include a background-and-object measurer 232 and an information acquirer 234. Also, the controller 230 may further include a body type determiner 236 and may, additionally, further include a recommendation information provider 238. The aforementioned configurations 232 to 238 of the controller 230 may be a software module or a hardware module configured in the controller 230 or at least one processor of the controller 230.

For example, the controller 230 may include processing circuitry such as hardware including logic circuits, a hardware/software combination such as a processor executing software; or a combination thereof. For example, the processing circuitry may include, but is not limited to, a central processing unit (CPU), an arithmetic logic unit (ALU), a digital signal processor, a microcomputer, a field programmable gate array (FPGA), a System-on-Chip (SoC) a programmable logic unit, a microprocessor, or an application-specific integrated circuit (ASIC), etc.

The processing circuitry may execute instructions stored in the memory to configure the processing circuitry as special purpose processing circuitry to perform the operations of the background-and-object measurer 232, the information acquirer 234, the body type determiner 236 and the recommendation information provider 238. Therefore, the processing circuitry may improve the functioning of the electronic device 100 itself by providing an easy way for users to identify the background 120 and the object 110 included in a subject based on data acquired from the sensor unit 210 while, at the same time, securing a high precision for determining a size of the object 110.

The controller 230 operating as the background-and-object measurer 232 may distinguish the object 110 from the background 120 based on data acquired/measured by the sensor unit 210, and may measure a distance from at least one measurement point among at least one point of the background 120 and at least one point of the object 110 to the electronic device 100, that is, the sensor unit 210.

The controller 230 operating as the information acquirer 234 may acquire information on a shape of at least one portion constituting the object 110 based on the distance measured by the background-and-object measurer 232. When the object 110 corresponds to a body, the information acquirer 234 may acquire part shape information on at least one of a shape, a length, and a width of at least a portion of a body part corresponding to the portion of the object 110.

The controller 230 operating as the body type determiner 236 may determine a body type of the body based on the part shape information acquired by the information acquirer 234.

The controller 230 operating as the recommendation information provider 238 may provide recommendation information on at least one item among clothes and accessories wearable to at least one part of the body based on the part shape information acquired by the information acquirer 234.

Further detailed functions and operations of the configurations 232 to 238 included in the controller 230 are further described with reference to FIGS. 3 to 10.

As discussed above, the configurations 232 to 238 of the controller 230 may be configured within at least one processor and accordingly, the functions and operations of the configurations 232 to 238 may be executed by at least one processor.

The server 130 may refer to a server or other computing devices configured to provide the electronic device 100 with recommendation information on an item suitable for the object 100 based on the acquired information on the shape associated with the object 110 or item information included in the recommendation information. The server 130 may include at least one database and other computing devices configured to store data required to provide the recommendation information to the electronic device 100. Meanwhile, although not illustrated, the server 130 may include a processor configured to process data for providing recommendation information to the electronic device 100 and a communicator used for communication with the electronic device 100.

Referring to FIG. 2, the server 130 may include an item information database 250 and a statistical information database 260.

For example, the server 130 may include a memory device such as a hard disk drive (HDD), a solid state drive (SSD), a random access memory (RAM), or any other suitable volatile, non-volatile, or combination of volatility and non-volatility memory device. The memory device may be configured to operate as the item information database 250 and a statistical information database 260.

The item information database 250 may store information on an item wearable by the object 110 in association with the object 110. When the object 110 is a body, the item information database 250 may store information on clothes and accessories wearable to the body. For example, the item information database 250 may store information on at least one of measurements (e.g., actual measurements), sizes (e.g., small, medium, large, etc.), and prices of the clothes and accessories, and images of the clothes and the accessories.

The server 130 may acquire information on the item through a server operated by an entity (e.g., a shopping mall, an advertising website, etc.) that sells, promotes, advertises, or reviews the item associated with information stored in the item information database 250, and may store the acquired information in the item information database 250.

The statistical information database 260 may store statistical information available to determine recommendation information that is to be provided to the electronic device 100. For example, when the object 110 is a body, the statistical information database 260 may store at least one of statistical (or demographical) body type information (e.g., information on an average weight and/or average height) on a body of a person, style information (information on a statistically preferred fit or style), fashion information (information on a statistically preferred item), and trend information (trend information on a preferred item or style).

The server 130 may acquire the statistical information through communication with a server operated by an entity (e.g., a national statistical office or the press) that provides data associated with information stored in the statistical information database 260, and may store the acquired information in the statistical information database 260.

The server 130 may provide recommendation information on an item most suitable for the electronic device 100 by referring to data stored in the item information database 250 and the statistical information database 260.

In the meantime, the item information database 250 and the statistical information database 260 may be configured into a single database, which differs from FIG. 2.

A method of providing recommendation information to the electronic device 100 is further described with reference to FIGS. 6 and 10.

Descriptions related to technical features described above with reference to FIG. 1 may apply to FIG. 2 and thus, repetitive descriptions are omitted.

Figure 3:
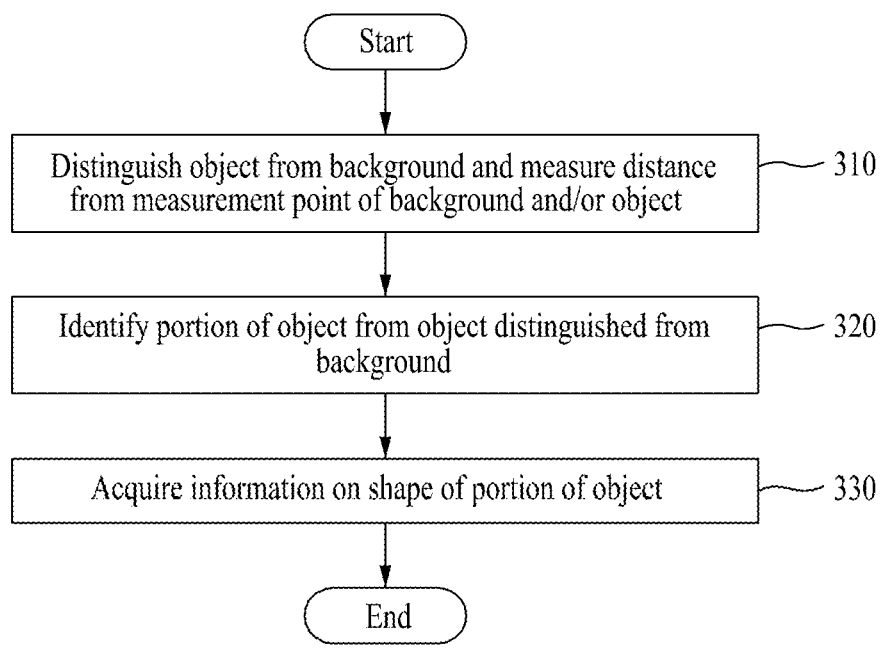
FIG. 3 is a flowchart illustrating a method of acquiring information on a shape of an object according to an example embodiment.
Figure 4:
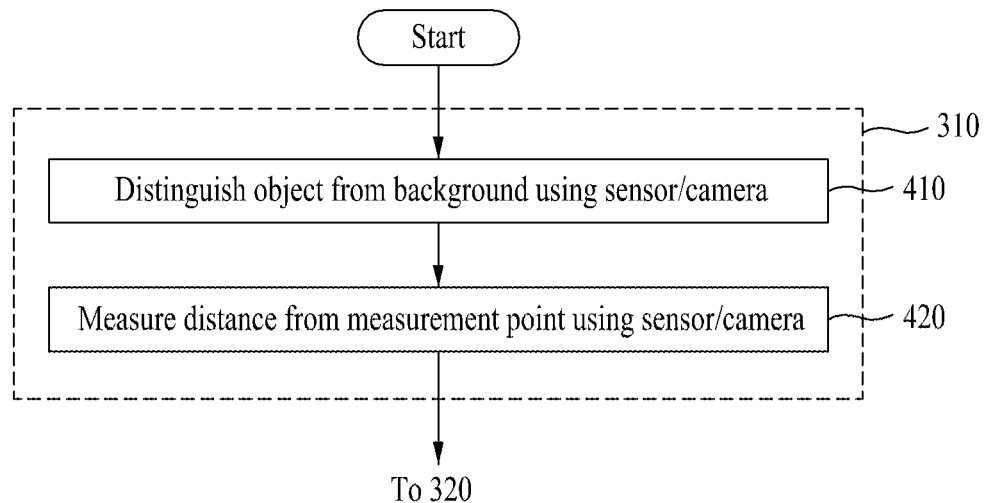
FIG. 4 is a flowchart illustrating a method of distinguishing an object from a background and measuring a distance from a measurement point of the background and/or the object, using a sensor unit according to an example embodiment.

FIG. 3 is a flowchart illustrating a method of acquiring information on a shape of an object according to an example embodiment, and FIG. 4 is a flowchart illustrating a method of distinguishing an object from a background and measuring a distance from a measurement point of the background and/or the object, using a sensor unit according to an example embodiment.

Hereinafter, a method of distinguishing the object 110 from the background 120, measuring a distance based on a measurement point of the object 110 and/or the background 120, and acquiring information on a shape of a portion of the object 110 using the aforementioned electronic device 100 is further described with reference to FIGS. 3 and 4.

Referring to FIG. 3, in operation 310, the controller 230 operating as the background-and-object measurer 232 may distinguish the object 110 from the background 120 around the object 110 and may measure a distance from at least one measurement point among at least one point of the background 120 and at least one point of the object 110 to the electronic device 100 (i.e., the sensor unit 210), using the sensor unit 210. Operation 310 may include the following operations 410 and 420.

Referring to FIG. 4, in operation 410, the background-and-object measurer 232 may distinguish the background 120 and the object 110 from each other using a sensor and/or a camera included in the sensor unit 210.

For example, the background-and-object measurer 232 may distinguish the object 110 from the background 120 by verifying the background 120 and an outline of the object 110 using the depth sensor 212 included in the sensor unit 210. The background-and-object measurer 232 may determine the background 120 and the outline of the object 110 based on a depth image of the background 120 and the object 110 acquired using the depth sensor 210. Alternatively, the background-and-object measurer 232 may distinguish the object 110 from the background 120 by verifying the background 120 and the outline of the object 110 using the camera 218 included in the sensor unit 210. The background-and-object measurer 232 may determine the background 120 and the outline of the object 110 based on an image or a picture of the background 120 and the object 110 acquired using the camera 218.

In operation 420, the background-and-object measurer 232 may measure a distance (from the sensor unit 210) to the measurement point of the background 120 and/or the object 110 using the sensor and/or the camera included in the sensor unit 210. The measurement point may refer to a point of the background 120 or the object 100. That is, the background-and-object measurer 232 may measure a distance from an arbitrary point of the background 120 or the object 100.

For example, the background-and-object measurer 232 may measure a distance based on ToF from the measurement point using the distance sensor 214 included in the sensor unit 210. For example, the background-and-object measurer 232 may calculate (acquire) a distance from the distance sensor 214 to the measurement point based on a value that is acquired by multiplying a velocity of light emitted by the distance sensor 214 by the ToF from the distance sensor 214 to the measurement point acquired from the distance sensor 214. The light emitted by the distance sensor 214 may be an infrared ray. Alternatively, ToF of an ultrasound wave or ToF of other waves may be used instead of the ToF of the infrared ray.

A method of measuring, by the background-and-object measurer 232, a distance from the measurement point is further described with reference to FIG. 8.

In operation 320, the controller 230 operating as the information acquirer 234 may identify at least one portion constituting the object 110 from the object 110 that is distinguished from the background 120. For example, when the object 110 is a body, the information acquirer 234 may identify a part, such as a head, an arm, a leg, and a torso constituting the body, as the portion that constitutes the object 110.

The information acquirer 234 may identify at least one portion constituting the object 110 based on the outline of the object 110 or the image or the picture captured by the object 110, verified in operation 310.

While FIGS. 3 and 4 illustrate an embodiment in which the controller 230 performs operation 320 after operation 310, which may include operations 410 and 420, example embodiments are not limited thereto. For example, in some example embodiments, operation 320 may be performed between operations 410 and 420, which differs from FIGS. 3 and 4. Alternatively, operation 320 may be included in operation 310 as a portion of operation 310.

In operation 330, the controller 230 operating as the information acquirer 234 may acquire information on a shape of the identified at least one portion constituting the object 110 based on the distance to the measurement point measured in operation 310. The acquired information on the shape may include information on a size of the corresponding portion. Information on a size may include at least one of a length and a width of the portion. For example, when the object 110 is a body, the acquired information on a shape may include information on a length and/or a width of a part constituting the body.

Example embodiments in which the object 110 is a body and the aforementioned operations 310 and 330 are further described with reference to the following FIGS. 4 to 10.

Descriptions related to technical features described above with reference to FIGS. 1 and 2 may apply to FIGS. 3 and 4 and thus, repetitive descriptions are omitted.

Figure 5:
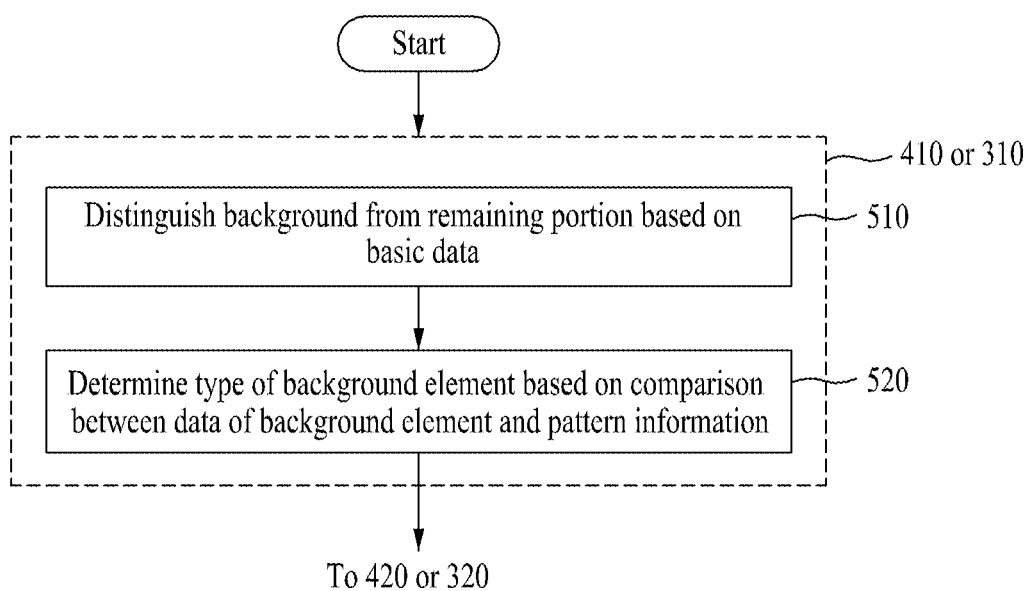
FIG. 5 is a flowchart illustrating a method of identifying a background element included in a background based on basic data according to an example embodiment.

FIG. 5 is a flowchart illustrating a method of identifying a background element included in a background based on basic data according to an example embodiment.

FIG. 5 illustrates in detail a method of distinguishing the object 110 from the background 120 in operations 310 and 410 described with reference to FIGS. 3 and 4.

Referring to FIG. 5, in operation 510, the background-and-object measurer 232 may distinguish the object 110 from the background 120 based on basic data. The basic data may be data used to further accurately distinguish the object 110 from the background 120. For example, the basic data may include at least one of position information representing a height (altitude) of the electronic device 100 that is acquired using the gyro/accelerometer sensor 216 and pattern information representing a pattern of a background element constituting the background 120. The pattern information may be set (or, alternatively, preset) in the electronic device 100 or may be provided from an external server and the like as preset information.

The background-and-object measurer 232 may distinguish the background element from a remaining portion of the background 120 based on at least one of information representing a height of at least one background element constituting the background 120 and the pattern information. Information representing the height of the background element may be determined based on position information representing a height (altitude) of the electronic device 100 acquired using the gyro/accelerometer sensor 216. The background element may include, for example, a floor, a ceiling, left/right wall and front. Alternatively, the background element may include an element, such as a door and a furniture, except for the object 110.

In operation 520, when a degree of matching between data represented the background element and the pattern information is greater than or equal to a desired value, the background-and-object measurer 232 may determine the background element as a set (or, alternatively, a preset) type background element. The type may include a door, a light, and furniture, in addition to a ceiling, a wall, and a floor.

For example, the background-and-object measurer 232 may determine a degree of matching between data acquired from the depth image acquired through the sensor unit 210 or the image or the picture acquired from the camera 218 and the pattern information.

Through operations 510 and 520, the background-and-object measurer 232 may distinguish elements of the background 120 from the object 110. Also, each of the elements (wall, furniture, etc.) of the background 120 may be identified.

The aforementioned basic data may be subsidiarity/additionally used in addition to the data acquired by the sensor unit 210 to further accurately distinguish the object 110 and the background 120.

The distinguished background elements are further described with reference to FIG. 7.

Descriptions related to technical features described above with reference to FIGS. 1 to 4 may apply to FIG. 5 and thus, repetitive descriptions are omitted.

Figure 6:
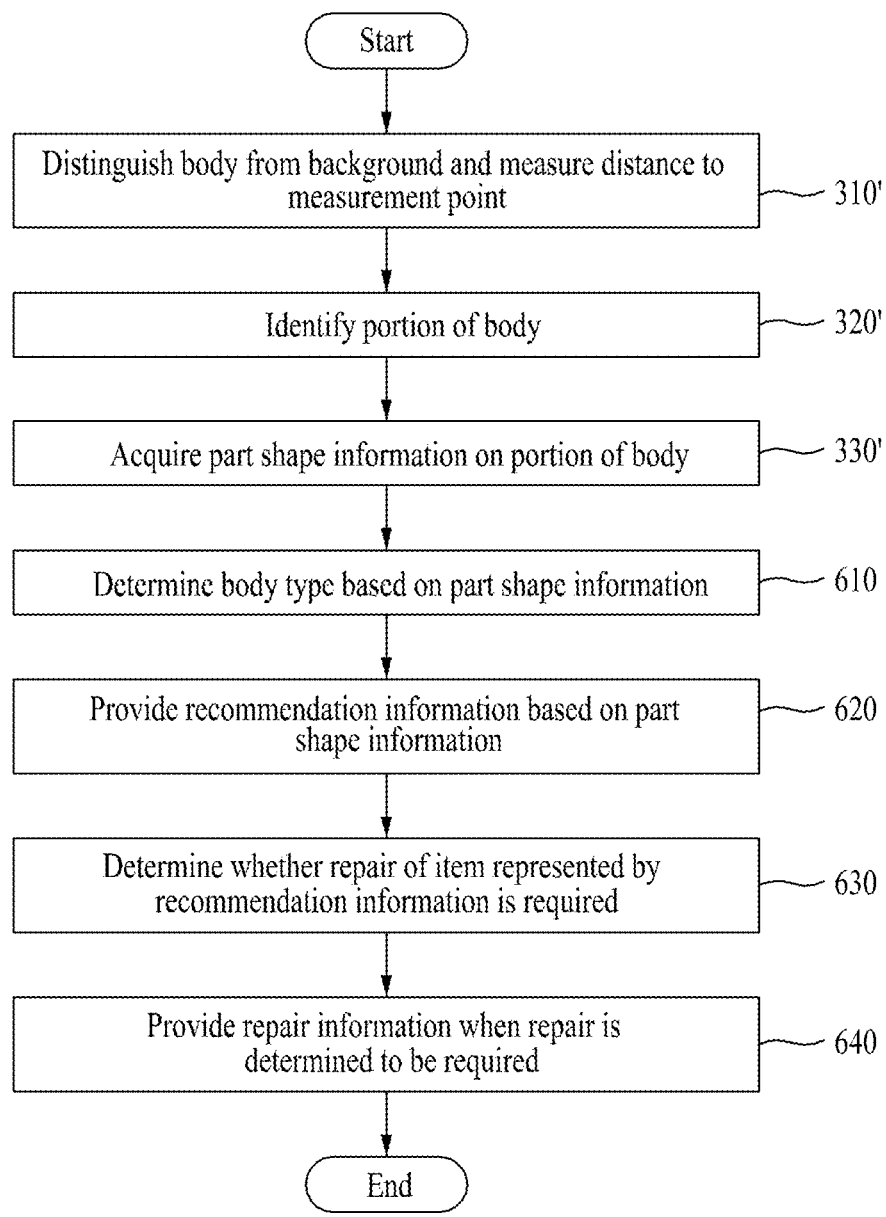
FIG. 6 is a flowchart illustrating a method of acquiring part shape information on a part of a body using a sensor unit and providing recommendation information on a suitable item based on the acquired part shape information according to an example embodiment.

FIG. 6 is a flowchart illustrating a method of acquiring part shape information on a part of a body using a sensor unit and providing recommendation information on a suitable item based on the acquired part shape information according to an example embodiment.

Hereinafter, an example embodiment in which the object 110 is a body is further described.

Referring to FIG. 6, in operation 310', the controller 230 operating as the background-and-object measurer 232 may distinguish the body from the background 120 around the object 110 and measure a distance from at least one measurement point among at least one point of the background 120 and at least one point of the body to the electronic device 100 (i.e., the sensor unit 210), using the sensor unit 210.

In operation 320', the controller 230 operating as the information acquirer 234 may identify at least one portion constituting the body from the body distinguished from the background 120.

In operation 330', the controller 230 operating as the information acquirer 234 may acquire part shape information on a shape of identified at least one part constituting the body based on the distance from the measurement point measured in operation 310'. The part shape information may include at least one of a shape, a length, and a width of at least one part constituting the body.

Descriptions related to operations 310 to 330 described above with reference to FIG. 3 may apply to the operations 310' to 330' of FIG. 6, respectively, and thus, repetitive descriptions are omitted.

In operation 610, the controller 230 operating as the body type determiner 236 may determine a body type of the body based on the part shape information acquired in operation 330'. The body type determiner 236 may determine the body type of the body by collectively considering part shape information acquired with respect to a plurality of parts constituting the body. For example, the body type determiner 236 may determine the body type of the body based on part shape information on at least two parts among the plurality of parts of the body. The body type determiner 236 may determine whether all of the sizes represented by the part shape information of the corresponding parts are greater than or equal to a desired value or whether all of a portion of the sizes are greater than or equal to the desired value and may determine the body type of the body. For example, the body type of the body may be determined to be one of body types including a skinny body, a normal body, and a large type (e.g., a plump body).

Alternatively, the body type determiner 236 may determine the body type of the body based on only part shape information on a desired (or, alternatively, a predetermined) part identified from among the plurality of parts of the body. Here, the determined body type of the body may represent a body type of the part (e.g., a slender face, a normal face, a wide (chubby) face, etc., with respect to a face).

The body type determiner 236 may determine the body type of the body by further considering the aforementioned statistical information stored in the statistical information database 260 of the server 130. For example, the body type determiner 236 may determine the body type of the body by further referring to average height information, average weight information, and information on a measurement of each part of the body stored in the statistical information database 260.

In operation 620, the controller 230 operating as the recommendation information provider 238 may provide recommendation information on at least one item for the body based on the part shape information acquired in operation 330'. The recommendation information may include information on clothes and/or accessories corresponding to a size (measurement, a width or a length, etc.) of a part of the body represented by the part shape information. For example, the recommendation information provider 238 may provide recommendation information on at least one item among clothes and accessories that are determined based on size information of a corresponding part that is determined based on the acquired part shape information. For example, the size information may represent a size, such as extra small, small, medium, large, and extra-large.

Also, the recommendation information provider 238 may provide recommendation information on at least one item among clothes and accessories determined based on the body type of the body determined in operation 610. That is, the recommendation information may include information on clothes and/or accessories determined based on the body type of the body verified by the electronic device 100. For example, when the body type is determined to be a skinny body, the recommendation information may include information representing clothes of a small size. When the body type is determined to be a plump body, the recommendation information may include information representing clothes of a large size.

Alternatively, the recommendation information provider 238 may provide recommendation information on at least one item among clothes and accessories determined based on statistical information associated with the determined body type of the body. For example, information on an item that is determined by applying at least one of demographic statistical information, style information, fashion information, and trend information associated with the determined body type of the body may be included in the recommendation information. For example, information representing highly popular clothes and/or accessories based on the determined body type may be included in the recommendation information. Here, when the body type is determined to be a skinny body, the recommendation information may include information representing clothes highly popular for the skinny body, such as clothes of a skinny jean or a horizontally striped design. When the body type is determined to be a plump body, the recommendation information may include information highly popular for the plump body, such as clothes of a box T-shirt or a vertically striped design.

Alternatively, the recommendation information provider 238 may provide recommendation information on at least one item among clothes and accessories determined based on a style setting set (or, alternatively, preset) by the user using the electronic device 100. For example, when the user sets a preferred style as a tight style, the recommendation information provider 238 may provide recommendation information including information on clothes such as a skinny jean.

An item represented by recommendation information may include clothes, such as top or bottom including an outerwear and an underwear and wearable accessories, such as a hat, shoes, sunglasses, a necklace, earrings, and the like.

The recommendation information may be provided to the user in a form in which an item represented by the recommendation information is worn to the body. For example, the user may verify a state in which the item represented by the recommendation information is worn to the body through the display 240 of the electronic device 100 or a user terminal of the user. That is, a virtual fitting service for the item may be provided to the electronic device 100 or the other user terminal of the user.

For example, the controller 230 may generate a virtual human model of the user based on information, such as a height, a weight, a gender and/or an age of the user, gathered from the sensor unit 210 and/or input manually by the user. The controller 230 may generate the virtual human model of the user such that the virtual human model is three-dimensional (3D). The controller 230 may fit the item on the virtual human model of the user in, for example, the 3D space such that the user is able to rotate the virtual human model in the 3D space to view the item from multiple perspectives.

Alternatively, items represented by the recommendation information may be provided in a form of a list. Alternatively, an item most suitable for the body or an item of a high popularity may be displayed in a state worn to the body and at least one candidate item may be separately provided in a form of a list.

Information on the item represented by the recommendation information may be acquired from the aforementioned item information database 250 of the server 130. In the meantime, demographic statistical information, style information, fashion information, and trend information associated with the body type may be acquired from the statistical information database 260 of the server 130.

In operation 630, the controller 230 operating as the recommendation information provider 238 may compare a measurement of the item represented by the recommendation information and part shape information and may determine whether repair of the corresponding item is required. The measurement of the item represented by the recommendation information may be acquired from the item information database 250. The measurement of the item may be an actual measurement of the corresponding item. Alternatively, the measurement of the item may use a general measurement value of the same type item corresponding to a size.

In some example embodiments, the recommendation information provider 238 may determine whether to repair the item based on a style setting that is preset by the user through the electronic device 100. For example, when the user sets a rollup (rolling up trouser legs or sleeves) style as a preferred style, the recommendation information provider 238 may determine that repair is not required although a measurement of sleeves or trouser legs of clothes represented by recommendation information is greater than a length represented by part shape information.

In operation 640, the recommendation information provider 238 may provide repair information on the item when the repair is determined to be required. The repair information may be provided to the user in a form in which the item represented by the recommendation information is worn to the body. For example, repair information may be visually provided as a simulation using the display 240 of the electronic device 100 and the user may verify a portion that needs to be repaired and a level of repair with respect to the item of which repair is required, through the display 240.

A method of providing repair information is further described with reference to FIG. 10.

Descriptions related to technical features described above with reference to FIGS. 1 to 5 may apply to FIG. 6 and thus, repetitive descriptions are omitted.

Figure 7:
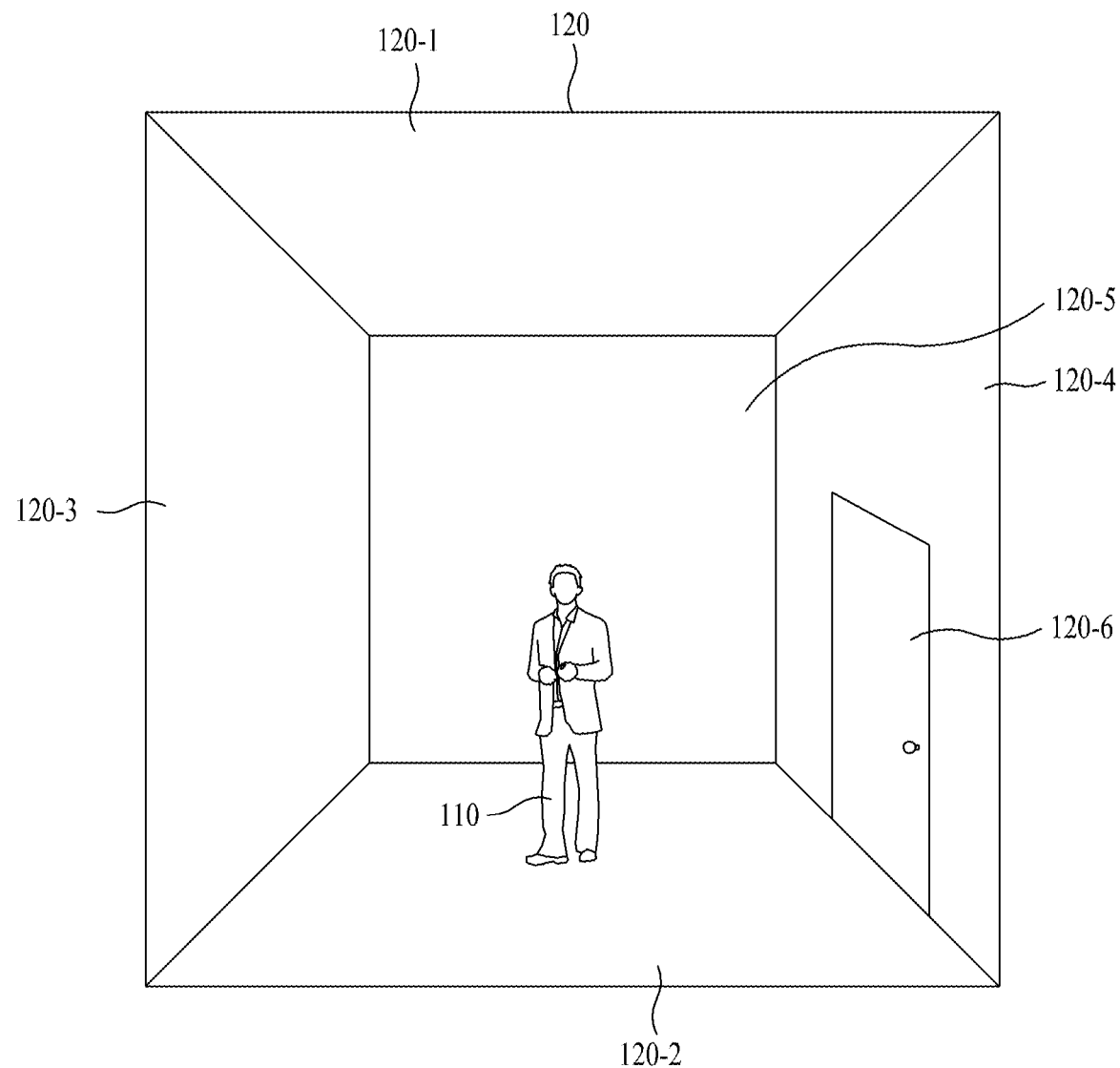
FIG. 7 illustrates a method of distinguishing an object from a background around the object according to an example embodiment.

FIG. 7 illustrates a method of distinguishing an object from a background around the object according to an example embodiment.

Referring to FIG. 7, the background 120 may include a plurality of background elements 120-1 to 120-6 and the object 110.

For example, the background elements may include a ceiling 120-1, a floor 120-2, a left wall 120-3, a right wall 120-4, and a front 120-5. Also, a thing, such as a door 120-6 or furniture, may be included in the background elements. However, example embodiments are not limited thereto, and the background 120 may include various ones of the plurality of plurality of background elements 120-1 to 120-6 or other background elements that are distinguishable from the object.

The controller 230 operating as the background-and-object measurer 232 may verify the background 120 and an outline of the object 110 using a sensor/camera included in the sensor unit 210, and may distinguish the background elements 120-1 to 120-6 of the background 120 from one another.

As described above with reference to FIG. 5, the background-and-object measurer 232 may distinguish the background elements 120-1 to 120-6 of the background 120 from one another based on pattern information. For example, the pattern information may include information on a general shape (e.g., a door corresponds to a rectangular shape) or a general measure corresponding to each background element. The background-and-object measurer 232 may determine a degree of matching between data represented by a background element and set (or, alternatively, preset) pattern information and may determine a type of the background element.

The controller 230 operating as the information acquirer 234 may acquire information on a shape of a portion constituting the object 110 using a relative size (length or width) of the background element distinguished from the background 120 and a depth value that is acquired from a depth image generated by the sensor unit 210. That is, the information acquirer may calculate a size of a portion constituting the object 110 using a relationship between the depth value and the relative size of the background element and may acquire the calculated size as information on the shape. The relative size of the background element may be subsidiarity/additionally used with respect to a method of acquiring information on the shape in operation 330.

Descriptions related to technical features described above with reference to FIGS. 1 to 6 may apply to FIG. 7 and thus, repetitive descriptions are omitted.

Figure 8:
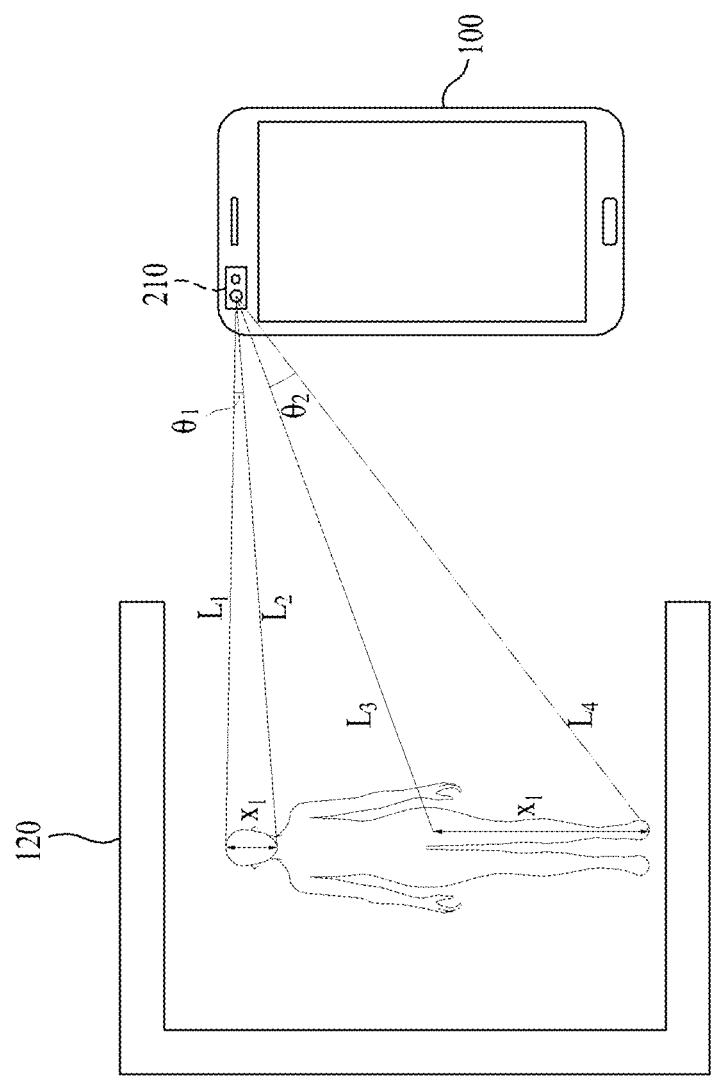
FIG. 8 illustrates a method of measuring a distance from a measurement point of each of a background and an object according to an example embodiment.

FIG. 8 illustrates a method of measuring a distance from a measurement point of each of a background and an object according to an example embodiment.

Referring to FIG. 8, the controller 230 operating as the information acquirer 234 may determine, as measurement points, both ends (e.g., ends of both sides for measuring a length or a width of a portion) of an identified portion of the object 110, may calculate a distance between the measurement points using distances between the measurement points and the sensor unit 210 measured through the background-and-object measurer 232 and an angle of view formed by straight lines that connect the sensor unit 210 from the measurement points, and may acquire the length or the width of the identified portion as information on the shape.

For example, with respect to measurement points of both ends of a head portion and measurement points of both ends of a right leg of the object 110, the background-and-object measurer 232 may measure distances from the sensor unit 210 to the measurement points using the sensor unit 210. The information acquirer 234 may calculate (acquire) a length $X_1$ of a head as information (i.e., part shape information) on a shape of the head using lengths $L_1$ and $L_2$ and an angle of view $\theta_1$ that are measured for the head. Also, the information acquirer 234 may calculate a length $X_2$ of the right leg as information (i.e., part shape information) on a shape of the right leg using lengths $L_3$ and $L_4$ and an angle of view $\theta_2$ that are measured for the right leg.

That is, the background-and-object measurer 232 may measure distances from two measurement points of a portion constituting the object 110 to the sensor unit 210, and the information acquirer 234 may acquire information on a shape of the portion by acquiring information on a size of the portion constituting the object 110 based on angles (e.g., corresponding to an angle of view) located in association with the measurement points and the measured distances using the sensor unit 210.

Alternatively, although not illustrated, the information acquirer 234 may calculate a length or a width of the identified portion of the object 110 using a ratio of the length or the width of the identified portion of the object 110 with respect to the distance(s) from the measurement point(s) measured in operation 310 or a relative size of the length or the width of the identified portion, and may acquire the calculated value as information on the shape of the corresponding portion.

Descriptions related to technical features described above with reference to FIGS. 1 to 7 may apply to FIG. 8 and thus, repetitive descriptions are omitted.

Figure 9:
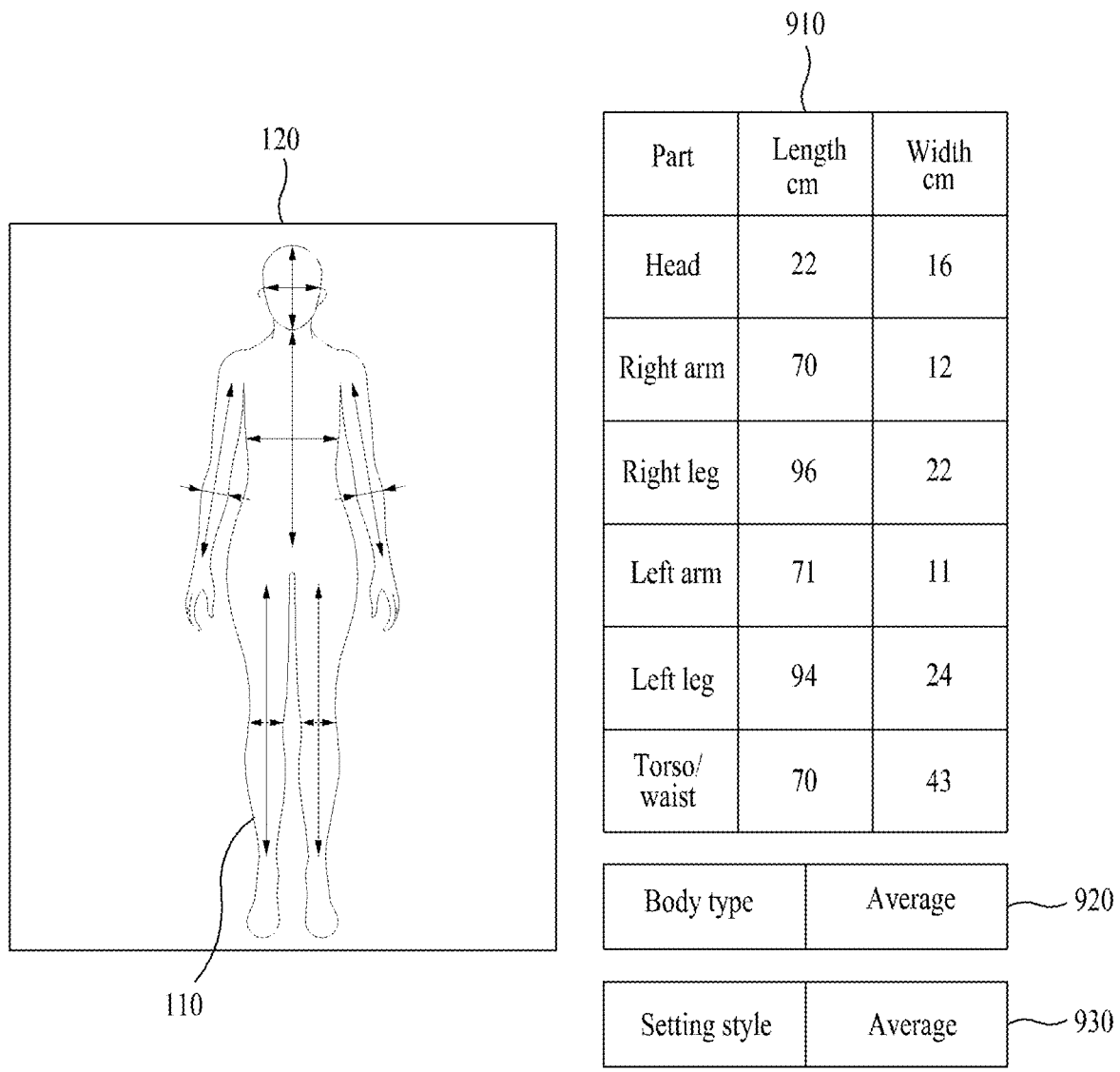
FIG. 9 illustrates part shape information on each of parts of an object corresponding to a body according to an example embodiment.

FIG. 9 illustrates part shape information on each of parts of an object corresponding to a body according to an example embodiment.

Referring to FIG. 9, part shape information 910 may be acquired through the method of the aforementioned example embodiments, body type information 920 may be determined based on the part shape information 910, and style setting information 930 may be set (or, alternatively, preset) by the user when the object 110 is a body.

The part shape information 910 may include a length and a width of the body. The body type determiner 236 may determine a body type of the body based on the part shape information 910. In the example, the body type of the body is determined to be average. In addition, the body type of the body may be determined to be a skinny body or a plump body based on a value of the part shape information 910. Here, data stored in the statistical information database 260 may be used to determine the body type.

In the example, the style setting information 930 is set to be average by the user. In addition, a tight style, a slim style, and a loose style may be set. As described above, the style setting information 930 may be used to determine an item recommended based on recommendation information or to determine whether repair is required in providing repair information.

Descriptions related to technical features described above with reference to FIGS. 1 to 8 may apply to FIG. 9 and thus, repetitive descriptions are omitted.

Figure 10:
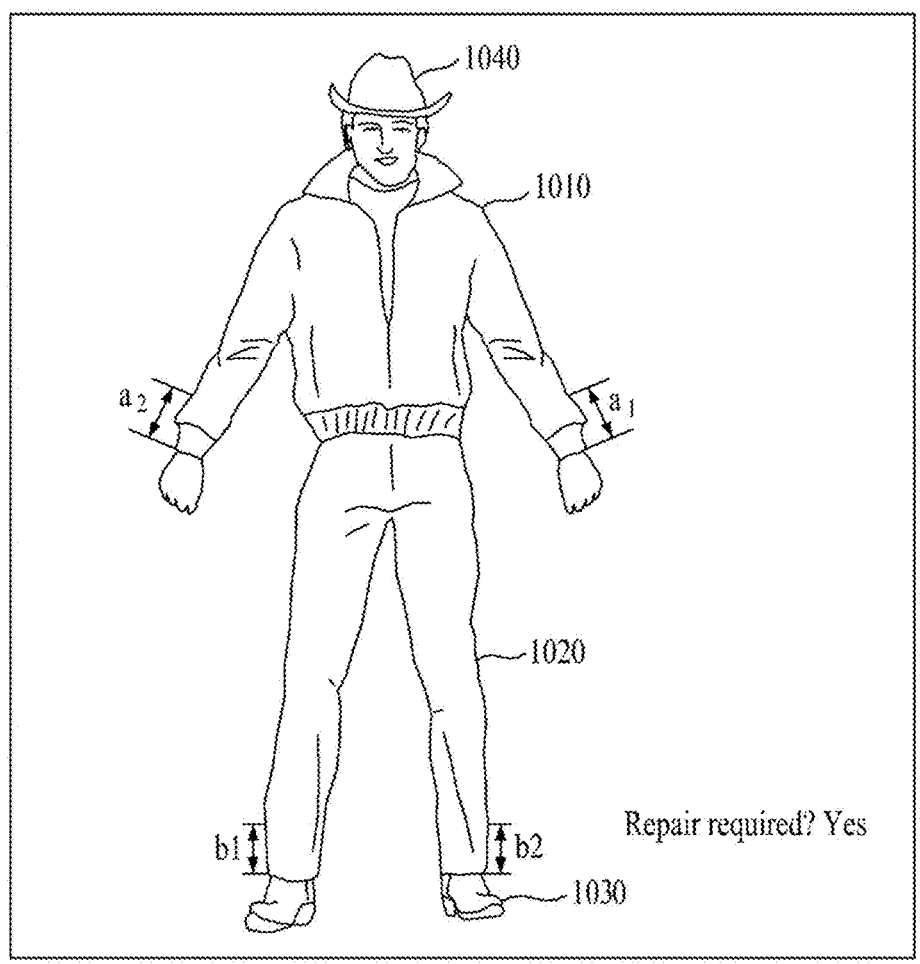
FIG. 10 illustrates a method of providing recommendation information and repair information on a suitable item based on acquired part shape information according to an example embodiment.

FIG. 10 illustrates a method of providing recommendation information and repair information on a suitable item based on acquired part shape information according to an example embodiment.

Referring to FIG. 10, recommendation information may be provided to the user in a form in which one or more of items 1010 to 1040 represented by the recommendation information is worn to the body. The user may verify a state in which the item represented by the recommendation information is worn to the body as a simulation through the display 240 of the electronic device 100.

In the illustrated example, the controller 230 operating as the recommendation information provider 238 determines that there is a need to repair a portion, for example, the items 1010 and 1020, among recommended items. Referring to FIG. 10, repair information may be visually provided as a simulation through the display 240 of the electronic device 100, and the user may verify a portion that needs to be repaired and a level of repair with respect to the item of which repair is required, through the display 240. In the example, it is determined that the top 1010 needs to be repaired by $a_1$ and $a_2$, and the bottom 1020 needs to be repaired by $b_1$ and $b_2$.

As described above, whether the repair is required may be determined based on a result of comparing a measurement of an item represented by recommendation information and acquired part shape information, and additionally/alternatively determined based on a style setting set (or alternatively, preset) by the user through the electronic device 100.

Descriptions related to technical features described above with reference to FIGS. 1 to 9 may apply to FIG. 10 and thus, repetitive descriptions are omitted.

In the aforementioned example embodiments, the body may need to be in a nude state or in an underwear state at a time of measuring a part of the body and acquiring part shape information. Here, when clothes and/or accessories are worn to the body at a time of measuring the part of the body and acquiring the part shape information, an operation of estimating a state of the body to which the worn clothes and/or accessories are detached may need to be performed in advance. Alternatively, the controller 230 may additionally perform a compensation operation for the worn clothes and/or accessories at a time of acquiring the part shape information.

Also, when measuring the part of the body, the controller 230 may prompt the user to be measured to take an easily measurable pose (e.g., a pose of spreading arms and legs to the full extent).

The apparatuses described herein may be implemented using hardware components, software components, and/or a combination thereof. For example, the apparatuses and the components described herein may be implemented using one or more processors such as, for example, a processor, a controller, an arithmetic logic unit (ALU), a digital signal processor, a microcomputer, a field programmable gate array (FPGA), a programmable logic unit (PLU), a microprocessor, or any other device capable of responding to and executing instructions in a defined manner to transform the processor into a special purpose computer. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will be appreciated that a processing device may include multiple processing elements and/or multiple types of processing elements. For example, a processing device may include multiple processors or a processor and a controller. In addition, different processing configurations are possible, such as parallel processors.

The software may include a computer program, a piece of code, an instruction, or some combination thereof, for independently or collectively instructing or configuring the processing device to operate as desired. Software and/or data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more computer readable record mediums.

The methods according to the above-described example embodiments may be recorded in non-transitory computer-readable storage media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable storage media include magnetic media such as hard disks, floppy disks, and magnetic tapes; optical media such as CD-ROM discs, and DVDs; magneto-optical media such as floptical disks; and hardware devices that are specially configured to store and perform program instructions, such as read-only memory (ROM), random access memory (RAM), flash memory, and the like. The media may be various recording devices or storage devices in which a single piece or a plurality of pieces of hardware are combined and may be present on a network without being limited to a medium directly connected to a computer system. Examples of program instructions include both machine code, such as produced by a compiler, and files containing higher level code that may be executed by the computer using an interpreter.

While this disclosure includes specific example embodiments, it will be apparent to one of ordinary skill in the art that various alterations and modifications in form and details may be made in these example embodiments without departing from the spirit and scope of the claims and their equivalents. For example, suitable results may be achieved if the described techniques are performed in a different order, and/or if components in a described system, architecture, device, or circuit are combined in a different manner, and/or replaced or supplemented by other components or their equivalents.

Therefore, the scope of the disclosure is defined not by the detailed description, but by the claims and their equivalents, and all variations within the scope of the claims and their equivalents are to be construed as being included in the disclosure.

What is claimed is:

1. A method of acquiring information on a shape of an object, the method comprising:
   distinguishing, via at least one sensor, the object from a background around the object, the distinguishing including determining a background element within the background as one of a plurality of set types of background elements in response to a degree of matching between data represented by the background element and pattern information of the one of the plurality of set types of background elements being greater than or equal to a desired value;
   measuring, via the at least one sensor, a distance from at least one measurement point among at least one point of the background and at least one point of the object to the at least one sensor; and
   acquiring information on a shape of at least one portion of the object based on at least the distance.

2. The method of claim 1, wherein the at least one sensor includes a depth sensor, and the distinguishing comprises:
   distinguishing the object from the background by verifying the background and an outline of the object using the depth sensor.

3. The method of claim 1, wherein the at least one sensor includes a distance sensor, and the measuring comprises:
   measuring the distance based on a time of flight (ToF) from the measurement point using the distance sensor.

4. The method of claim 1, wherein the information on the shape includes a size of the portion,
   the measuring includes measuring distances from a plurality of measurement points of the portion to the at least one sensor, and
   the acquiring includes acquiring information on the size of the portion based on angles associated with the plurality of measurement points and the distances from the plurality of measurement points to the at least one sensor.

5. The method of claim 4, wherein the information on the size of the portion includes at least one of a length and a width of the portion.

6. The method of claim 1, wherein the distinguishing comprises:

distinguishing the background element from the remaining portion of the background based on at least one of a height of at least one background element of the background and the pattern information.

7. The method of claim 1, wherein the object is a body, the portion is a part of the body, and the information on the shape indicates at least one of a shape, a length, and a width of at least the part of the body.

8. The method of claim 7, further comprising:

determining a body type of the body based on the information on the shape.

9. The method of claim 8, wherein the body includes a plurality of parts, and the determining of the body type comprises:

determining the body type of the body based on the information on the shape of at least two parts among the plurality of parts and the information on the shape of a predetermined part among the plurality of parts.

10. The method of claim 7, further comprising:

providing recommendation information on at least one item among clothes and accessories wearable to the part, based on the information on the shape.

11. The method of claim 10, wherein the providing of the recommendation information comprises:

providing the recommendation information on the at least one item based on a body type of the body, the body type determined based on the information on the shape.

12. The method of claim 11, wherein the providing of the recommendation information comprises:

providing the recommendation information on the at least one item based on statistical information associated with the body type of the body.

13. The method of claim 10, wherein the providing of the recommendation information comprises:

providing the recommendation information on at least one item based on size information of the part, the size information being determined based on the information on the shape.

14. The method of claim 13, further comprising:

determining whether to recommend repair of the item by comparing a measurement of the item and the information on the shape; and providing repair information on the item in response to determining to recommend the repair.

15. The method of claim 14, wherein the determining whether to recommend the repair of the item is based on style information set by a user.

16. A non-transitory computer-readable record medium storing a program that, when executed by processing circuitry, configures the processing circuitry to perform the method of claim 1.

17. An electronic device comprising:

at least one sensor; and processing circuitry configured to, distinguish, via the at least one sensor, an object from a background around the object by determining a background element within the background as one of a plurality of set types of background elements in response to a degree of matching between data represented by the background element and pattern information of the one of the plurality of set types of background elements being greater than or equal to a desired value, measure a distance from at least one measurement point among at least one point of the background and at least one point of the object to the at least one sensor, and acquire information on a shape of at least one portion of the object based on at least the distance.

18. The electronic device of claim 17, wherein the object is a body, the portion is a part of the body, and the information on the shape includes at least one of a shape, a length, and a width of at least a portion of the part, and the processing circuitry is further configured to, determine a body type of the body based on the information on the shape.

19. The electronic device of claim 17, wherein the object is a body, the portion is a part of the body, and the information on the shape includes at least one of a shape, a length, and a width of at least the part of the body, and the processing circuitry is further configured to, provide recommendation information on at least one item among clothes and accessories wearable to the part of the body, based on the information on the shape.

* * * * *